United States Patent [19]

Arima et al.

[11] 4,330,527

[45] May 18, 1982

[54] WOUND TREATMENT AGENT

[76] Inventors: Teruo Arima, No. 53-10, 6-chome, Tsukaguchi-cho, Amagasaki-shi, Hyogo-ken; Kenji Machii, No. 4-45-404, 3-chome, Takabedai, Tondabayashi-shi, Osaka-fu; Nobumoto Chikazawa, No. 5016-29, Nakamachi, Nara-shi; Tetsuya Takeuchi, No. 7-7, Tsukumodai, Suita-shi, Osaka-fu; Setsuro Fujii, No. 4-27-131, 1-chome, Nishimidorigaoka, Toyonaka-shi, Osaka-fu, all of Japan

[21] Appl. No.: 93,530

[22] Filed: Nov. 13, 1979

[51] Int. Cl.³ .............................................. A61K 37/48
[52] U.S. Cl. ..................................... 424/94; 424/145
[58] Field of Search ........................... 424/94; 435/194

[56] References Cited

U.S. PATENT DOCUMENTS 4,152,209  5/1979  Nishino et al. ...................... 435/194

Primary Examiner—Sam Rosen
Attorney, Agent, or Firm—Birch, Stewart, Kolasch & Birch

[57] ABSTRACT

A new wound treatment agent which contains as an effective ingredient a fraction containing nucleoside phosphotransferase produced by a nucleoside phosphotransferase producing bacterium belonging to the genus Clostridium, solely or in combination with zinc oxide.

12 Claims, 9 Drawing Figures

Effects of GF-70 on DNA and RNA Contents of Subcutaneously Inplanted P.V.H Sponge Additional Effects of ZnO into GF-70 Ointment on the Wound Healing in Rat
( by means of wound area method )

A ■ Ointment only
B ☐ 5% ZnO + GF-70 Ointment
C ☐ 10% ZnO + GF-70 Ointment
D ☐ 20% ZnO + GF-70 Ointment GF-70      Control

WOUND TREATMENT AGENT

BACKGROUND OF THE INVENTION

1. Field of the Invention

The present invention relates to a new wound treatment agent which contains as an essential, effective ingredient, a fraction containing nucleoside phosphotransferase obtained from a broth of a nucleoside phosphotransferase producing bacterium belonging to the genus Clostridium, solely or in combination with zinc oxide.

2. Description of the Prior Art

Already in practical use are wound treatment agents such as boric acid/zinc oxide ointment, zinc oxide ointment, Solcoseryl ointment, which are efficacious for various kinds of skin lesions, with the characteristic effects of the effective ingredients contained. Zinc oxide shows protective action, mild astringency and weak antisepsis. The extracted component derived from calves contained in Solcoseryl ointment has a marked tissue respiration stimulating action. Vitamin A acts to affect the growth and differentiation of skin tissues and to stimulate the synthesis of DNA in epidermis, and, chlorhexidine exhibits bactericidal action.

Yet, from the standpoint of the prevention of wound infection, it is required that the wound treatment agent have an excellent effect in stimulating granulation and epidermization, and to be useful in the treatment of different stages of a wide variety of localized and generallized skin lesions.

SUMMARY OF THE INVENTION

The present invention has been completed with a specific view to meeting with the above requirement, and has as a main object to provide a new wound treatment agent with a greatly improved therapeutic effect in comparison to the therapeutic effects of conventional wound treatment agents.

DETAILED DESCRIPTION OF THE INVENTION

Figure 1:
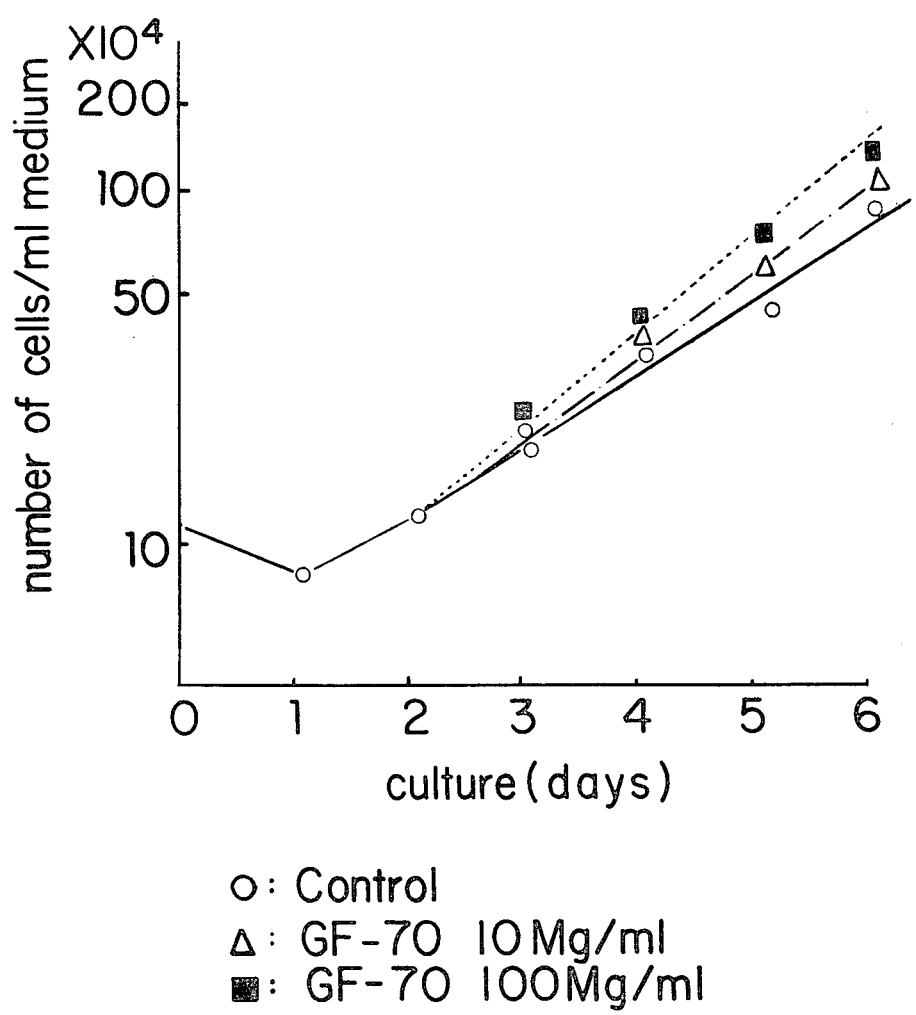
FIG. 1 is a graph showing the effects of GF-70 on the growth of the above mentioned BHK-21 cells.

The present invention relates to new wound treatment agents, and more particularly to new wound treatment agents which stimulates granulation and epidermization in the wounded area and preparations which contain as a main component a fraction of nucleoside phosphotransferase (hereinafter called "GF-70") produced by an anaerobic bacillus belonging to the genus Clostridium and preparations which further contain zinc oxide.

The objective of the present invention lies in the provision of a new wound treatment agent exhibiting greatly improved wound-therapeutic action with respect to conventionally known wound treatment agents.

Treatment of wounds is of vital importance for prevention of wound infection not only in general traumas, anal fistula and decubitus but also after major operations in which the degree of the wounds extend far into the depths of the body. The important function or subject of a wound treatment agent is to stimulate granulation and epidermization in damaged areas during the process of therapy of these wounds. To this end, several kinds of wound treatment agents such as boric acid/zinc oxide ointment, zinc oxide ointment, Solcoseryl ointment (tradename—Tobishi Pharmaceutical Co., Ltd.) and AD ointment "Tokyo Tanabe" have currently come into practical use.

Referring to the characteristic features of these conventional wound treatment agents, the boric acid/zinc oxide ointment and zinc oxide ointment, containing zinc oxide which show locally protective action, mild astringency and weak antisepsis, are applied topically for efficacy in all phases of eczema, abrasio and other general skin diseases, blister, pustule, erosion, and ulcer. Solcoseryl ointment contains a component derived by extraction from calves, has a tissue respiration stimulating action, and is claimed to be effective in the promotion of granulation in the cases of decubitus, varicose ulcer, trauma, scald, burn and general surgical wounds. AD ointment, "Tokyo Tanabe", which contains as the effective ingredient vitamin A (10,000 IU/g-ointment), is intended to be directed toward wounds, abrasion, burn, scald, frostbite, skin ulcer and keratodermia, and is reputed for its efficacy as an agent for granulation and epidermization. Incidentally, vitamin A has been well known to affect the growth and differentiation of the skin tissue (Wolback, S. B. and Howe, P. R.; J. Exp. Med., 45, 753 (1925), Fell, H. B., Proc. Roy. Soc., B., 146, 242 (1957), and a report was made of the fact that vitamin A stimulates synthesis of DNA in the epidermis (Christophers, E. and Braun Falco, O.; Arch. Klin. Exper. Dermatol., 232, 427 (1968). In addition to the above, medicines having bactericidal effect (antibacterial action) such as an ointment containing chlorhexidine homologues are sometimes utilized.

Effects of medicine (efficacies) exhibited by different kinds of ointments as described above are varying to a wide extent, whereas the process of wound healing involves a physiologically, very complicated phenomenon. The process, when being roughly broken down for interpretation, may be viewed as a phenomenon in which various kinds of cells appear in turn to absorb foreign substances, destroy bacteria and restore the tissue. The phenomenon may be analyzed in more detail as follows. In the case of a deep wound, blood flows from an end of the ruptured bood vessel into a gap of tissues torn away, fills in the gap and forms thrombus for bonding the wound peripheries. The thrombus then loses its liquid component within several hours, becoming dry on the surface to form a crust which plays the role of providing protection for the wound surface. At the same time, the injured area accompanies the inflammation, which is initiated at the time when the body fluid flows within the wound surrounding the thrombus, along with the swelling and pain felt symptomatic thereof, which is followed by the wandering of varieties of leukocytes into the wound taking place about 6 hours after the wound is inflicted to thereby remove and decompose the destroyed cells, bacteria and other foreign materials afterwards, fibroblasts migrate into the wound and synthesize the collagen fibers and other proteins to thus form scar tissue inside the corium, while formed on the epidermis (or the outermost surface layer) is the surface similar to that of the epidermis before the wound has been inflicted. Upon almost complete formation of this layer, the crust exfoliates, leading to completion of the wound healing.

Although the wound healing process mentioned above has been fairly clarified histologically, it is yet to be elucidated thoroughly on the molecular level.

Under these circumstances, the present inventors have come up with the idea of applying to the wound a fraction of nucleoside phosphotransferase (hereinafter called "GF-70") prepared previously by Fujii, a co-inventor, from nucleoside-phosphotransferase producing bacteria such as Clostridium perfringens ATCC 21510. Nucleoside phosphotransferase (hereinafter called "NPT") is an enzyme which catalyzes the reaction of phosphorylation to a nucleoside with nucleoside monophosphates such as AMP: adenosine monophosphate as the phosphate donor. Fujii et al, with regard to germinating potatoes and microorganisms (bacteria of the genus Clostridium as above mentioned and Tetrahymena Pyriformis) clarified the the mechanism of the phosphorylation catalysis as well as the differences from thymidine kinase (T. Arima, M. Masaka, T. Shiosaka, H. Okuda and S. Fujii: Biochim. Biophys. Acta, 246, 184 (1971): T. Shiosaka, Y. Omura, H. Okuda and S. Fujii: ibid., 204, 352 (1970): T. Shiosaka, H. Okuda and S. Fujii: ibid., 246, 171 (1971)). These reports signify that NPT is an important enzyme capable of stimulating the rate of DNA synthesis just like the thymidine kinase existing in mammals.

As previously described, multiplication of cells, eventually with nucleic acid synthesis accompanying it, is necessary to restore tissues destroyed through wound infliction. The understanding that NPT is the rate-determining enzyme for synthesis of DNA indeed implies, in terms of the suggested possibility of the said enzyme stimulating DNA synthesis, some kind of relationship existing between the said enzyme and the wound healing action. On the other hand, the wound healing process has been hardly elucidated successfully on the molecular level as already reviewed. Consequently, the finding that the NPT fraction (GF-70) is efficacious for promoting the healing of experimental wound inflicted on animals may be able to be called an unexpected discovery. In any way, the present invention has been completed on the basis of the discovery that GF-70 possesses a strong granulation action as having been revealed by our synthetic investigation conducted on its effects on the proliferation and nucleic acid synthesis in injured areas from various viewpoints of a molecular level discussion, morphological observation and healing action for experimental wounds. To be below described are the details of the present invention and experimental facts providing the basis therefor.

The summary of the present invention lies in:

(1) a new wound treatment agent containing as the effective ingredient GF-70 produced by NPT producing bacteria belonging to the genus Clostridium, and (2) a new wound treatment preparation containing as effective ingredients; GF-70 produced by NPT producing bacteria belonging to the genus Clostridium, and zinc oxide.

What is herein called GF-70 is a fraction containing NPT produced, in accordance with the method as described in the specification of the Japanese Pat. No. 745940 (Japanese Patent Publication No. 6675-1974) owned by the present applicant, from a broth (bodies of bacteria and/or a filtrate of a culture medium) obtained by cultivating an NPT producing bacterium of the genus Clostridium, for example the ATCC 21510 strain of Clostridium perfringens, in a culture medium containing C source, N source and sources of other trace nutrient elements, under the conditions of, preferably, pH of around 8 and temperature in the vicinity of 37° C. for about 45 hours anaerobically, or bacteria bodies obtained by effecting cultivation under the same conditions for 4 hours, by employing solely or in combination the routine means for extraction and purification of proteins such as extraction, precipitation, dialysis, solvent fractionation, ammonium sulfate fractionation, chromatography, gel filtration and electrophoresis. Incidentally, NPT is contained in larger quantities in bacterium bodies than in a filtrate of a culture medium, and it is recommended for extraction to grind the bacterium bodies by ultrasonic wave treatment, a homogenizer, etc., or to destroy the bacterium bodies with a hypotonic solution, for extraction. In view of the fact that NPT is resistant to ordinary proteolytic enzymes (trypsin, chymotrypsin, Pronase (tradename), etc.), the utilization of an appropriate proteolytic enzyme during the steps of extraction and purification to digest proteins of the contaminated bacterium bodies simplifies the purification step. NPT thus isolated (believed to be pure) has the following physicochemical properties:

(1) Elementary analysis: C, 35.25%: H, 6.51% : N, 11.92%.

(2) Specific rotation: $[\alpha]_D + 20°$ (water)

(3) Appearance: White, powdered substance (4) Solubility: Soluble in water, but insoluble in organic solvents such as methanol, ethanol, acetone and ether.

(5) Molecular weight: 48000 (gel filtration method)

(6) Ultraviolet absorption spectra: Absorption: 280 nm (7) Infrared absorption spectra: Absorptions at 1300, 1550 and 1630 cm$^{-1}$ attributed to protein or amino acids are observed.

(8) Color reaction: Responds positively to protein color reaction tests such as xanthoproteic reaction, Pauli reaction, Sakaguchi reaction, Hunter reaction, Sullivan reaction, Hopkins-Cole reaction, nitrosonaphthol reaction, Millon's reaction, Neubauer-Rhode reaction and Liebermann reaction.

(9) Actions: Possesses the action of transferring a phosphoric acid of a nucleoside monophosphate as the phosphate donor in the mechanism of phosphoric acid transfer, to other nucleoside as the phosphate acceptor. It, at the same time, has the action of carrying out dephosphorylation of nucleotide as the phosphate donor, to nucleoside.

(10) Specificity for substrates: Various kinds of nucleoside monophosphates and nucleoside diphosphates can be mentioned as the substances acting as the phosphate donor. Such actions are not observed for adenosine triphosphate, deoxyadenosine triphosphate, 3-phosphoglycerophosphate, carbamyl phosphate, creatine phosphate, α-glycerophosphate and glucose-6-phosphate.

As the phosphate acceptor are mentioned thymidine, deoxyuridine, deoxycytidine, cytidine and uridine. Among them, uridine is of the lowest activity as the phosphate acceptor.

(11) Optimal pH and stable pH range: The optimal pH is 6.0 to 7.0, while the stable pH is in the range of 7.0 to 8.0. Therefore, a pH range of from 6.0 to 8.0 is useful.

(12) Optimal temperature range of action: 30° to 40° C.

(13) Conditions of inactivation by pH, temperature, etc.: Relatively unstable at pH 2 to 5, and almost inactivated at pH 1.2, at 30° C. for 16 hours.

As to the action of heat, it is relatively stable at 50° C. for 10 minutes, and almost inactivated at 60° C. for 10 minutes, whereby pH is at 7.0.

(14) Inhibition, activation and stabilization: Investigation on the effects of metal ions on the activity has revealed that nucleotidase is activated by $Mg^{++}$, $Co^{++}$, $Zn^{++}$ and $Cu^{++}$ but inhibited by $Cd^{++}$, $Sn^{++}$ and $Ca^{++}$, whereas NPT is inhibited by $Cd^{++}$, $Sn^{++}$ and $Ca^{++}$ similarly but activated markedly by $Mg^{++}$, etc. Regarding other chemical agents, both of NPT and 5'-nucleotidase are inhibited by 20 to 30% in the activity by sodium fluoride, whereas neither of them are inhibited by p-chloromercuribenzoic acid. 5'-nucleotidase activity is inhibited by all nucleosides present at a concentration of not less than 1 mM, and completely inhibited by it at a concentration of 8 mM.

(15) Crystal form: Amorphous powder.

(16) Electrophoretic characteristics: Mobility in a 10% polyacrylamide gel (pH 8.3) is $1.8 \times 10^{-5} cm^{-2} volt^{-1} sec^{-1}$ (the mobility of bromphenol blue migrated simultaneously is $5.0 \times 10^{-5} cm^{-2} volt^{-1} sec^{-1}$).

(17) Melting point: The present enzyme is protein, with no characteristic melting point observed. It softens at 200° C., followed by gradual blackening.

(18) Isoelectric point: The present enzyme has the isoelectric point at pI 5.0.

(19) Toxicity: With the use of groups each consisting of 10,5-week aged mice (male and female) of the SLC-ddy strain (SPF), observation was conducted over a 7-day period after administration, and the results on $LD_{50}$ calculated by the method of Litchfield-Wilcoxon are shown below:

| Sex | Administration route | $LD_{50}$ (95% confidence limits, mg/kg) |
|---|---|---|
| M | Intravenous | 320 (267 to 384) |
| F |  | 345 (261 to 455) |
| M | Subcutaneous | 950 (839 to 1075) |
| F |  | 860 (769 to 962) |

In bringing it into practical use, however, it is in no way required to purify the present enzyme to such an extent as to give a single electrophoretic band. As shown below in Table 1, the cultivated bacteria of Clostridium perfringens ATCC 21510, being converted into the acetone-dried bacteria, are purified as follows. An extract "(a)" is obtained through extracting with 5 mM Trishydrochloric acid buffer (pH 8.0). Extract (a) is mixed with trypsin at a ratio of 1 mg per 20 mg of crude protein and allowed to stand at 37° C. for 30 min., followed by fractionating with cold ethanol, yielding a fraction "(b)" (ethanol concentration—0→66%) the precipitate by fractionation of (b) is dissolved in the above mentioned buffer to fractionate with ammonium sulfate (concentration of ammonium sulfate is 50 to 95%), resulting in a product "(c)" the precipitate by fractionating with ammonium sulfate of (c) is dissolved again in a small amount of the same buffer and dialyzed against the same buffer with the use of a visking tube, followed by effecting a gel filtration with Sephadex G-200 column, resulting in a filtrate "(d)" the fraction of gel filtration (d) is stepwise eluted with DEAE-Sephadex A-25 column, while the concentration of potassium chloride added to the above mentioned buffer is stepwise increased from 0.01 to 0.5 M, yielding a eluted fraction "(e)". For each of these purification steps, the healing effect was examined on the experimental wound inflicted on guinea pigs, whereupon there has been observed the wound healing effect in the NPT active fractions.

The NPT activity in each of the purification steps (in terms of the thymidine phosphorylating activity) is determined by an in-vitro measuring means for enzyme activity with $[2-^{14}C]$ thymidine employed as the substrate and adenosine monophosphate as the donor, which implies the increase of the specific activity of NPT with each one purification step (please refer to the Table shown below).

TABLE 1

| Purification step | Total activity (μmoles) | Specific activity (μmoles/mg protein | Ratio (times) | Wound healing effect |
|---|---|---|---|---|
| a | 244 | 1.45 | 1.0 | +++ |
| b (0-66% fraction) | 217 | 5.38 | 3.7 | +++ |
| c (50-90% fraction) | 165 | 9.42 | 6.5 | +++ |
| d (fraction C) | 122 | 33.9 | 23.4 | +++ |
| e (fraction D*) | 57.7 | 76.7 | 52.9 | +++ |

Remarks:
*indicates an elecrophoretically single pattern.

Accordingly, the therapeutically effective component observed in the substances (or component of bacteria) produced by Clostridium perfringens ATCC 21510 is supposed to be derived from the sole action of NPT or combined action of NPT and other enzymes involved in the nucleic acid synthesis, and the efficacious fraction including all of those in the above mentioned purification steps, (a) to (e), is tentatively referred to as "GF-70". From the standpoint of conducting commercially the invention into practice, the degree of purification up to the step (b) or (c) may practically be sufficient, only if the production procedures may be as simple as possible, with the resulting NPT fraction retaining the efficacy and safety. Incidentally, the NPT activities indicated in the Table are examined with the following test method:

To 0.1 ml of a sample enzyme solution placed in a test tube are added 0.1 ml of a 0.5 M Tris-hydrochloric acid buffer (pH 7.0), 0.025 ml of a 0.1 M magnesium chloride, 0.1 ml of a 0.1 M adenosine monophosphate, 0.025 ml of a 0.001 M $[2-^{14}C]$thymidine (30000 cpm) and 0.15 ml of water, and the reaction is allowed to take place at 37° C. for 30 minutes, and to go to conclusion by immersing the tube in boiling water for 3 minutes the denatured protein is subjected to centrifugal precipitation (3000 rpm, for 5 minutes), 0.1 ml of the resulted supernatant liquid is applied to DEAE-cellulose paper (3 cm×3 cm), which is dried and immersed in about 0.001 M ammonium formate solution for 10 minutes and then in deionized water for 10 minutes. By repeating this procedure twice, the unreacted $[2-^{14}C]$thymidine is washed out, while the reaction product of

[2-$^{14}$C]thymidine monophosphate alone is permitted to be retained on the DEAE cellulose paper. The DEAE cellulose paper is dipped in ethanol, dried at 80° C., and placed in a counting vial containing 10 ml of a toluene-phosphorus mixture (100 mg of 1,4-bis-2,2-(5-phenyloxazole)benzene and 4 g of 2,5-diphenyloxazole in one liter of toluene). The radioactivity is counted by a liquid scintillation counter.

[Action and effect of GF-70]

Experiment 1. Accelerating effect of $^3$H-deoxyadenosine incorporation into BHK cells.

Renal fibroblasts of hamstars (BHK-21) are cultured on culture media containing different concentrations of GF-70 to measure the rate of $^3$H-deoxyadenosine ([$^3$H]Adr) incorporation or migration into DNA of the BHK cells. Incidentally, the GF-70 sample utilized in this experiment shows 10 μmoles/mg protein/30 min. of the specific activity as the thymidine phosphorylating activity, and corresponds approximately to the step (c) of Table 1. The results are as shown in Table 2.

TABLE 2

| Cultured cells | GF-70 concentration in culture media (μg/ml) | $^3$H-Adr incorporation into DNA of cells (cpm/total of DNA) | P* |
|---|---|---|---|
| BHK-21 | Isotonic saline solution | 3619 ± 863 | |
| | 0.1 | 5175 ± 1696 | 0.001 |
| | 1.0 | 6389 ± 1647 | 0.001 |
| | 10.0 | 6353 ± 1588 | 0.001 |

Remarks:
*statistical significance (t-test method)

As indicated above in Table 2, there is revealed the marked difference (P<0.001) as compared with the control reference at the GF-70 concentration level of 0.1 μg/ml. The incorporation reaches the maximum in the GF-70 concentration of 1 μg/ml, with no change in the effect observed at higher concentration levels (10 μg/ml). Therefore, concentrations of between 0.1–10 μg/ml are effective.

Experiment 2: Effects of GF-70 on the $^3$H-thymidine incorporation into nuclei of BHK-21 cells.

With the use of slides equipped with a tissue culture chamber, comparative study is made by radioautography to find out differences between the culture media with and without GF-70 content of 10 μg/ml.

Figure 4:
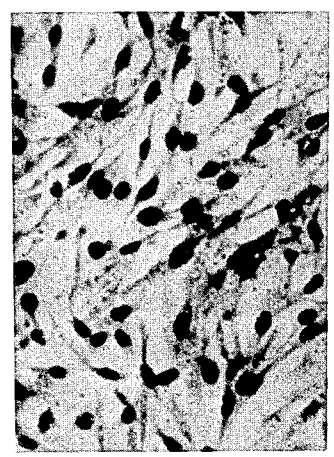
FIG. 4 is a photograph which shows that 3H thymidine incorporation into nuclei of BHK-21 cells becomes highly active through addition of GF-70.
Figure 4:
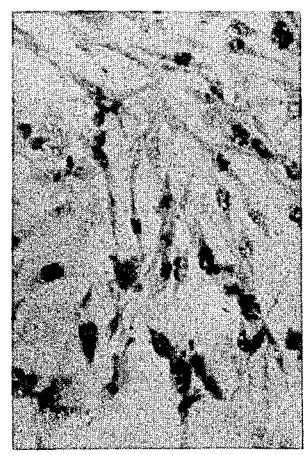

The fact can be seen that the $^3$H-thymidine incorporation into nuclei of BHK-21 cells has become highly active through addition of GF-70. (FIG. 4).

Experiment 3: Effects of GF-70 on the proliferation of the BHK-21 cells.

In culturing the BHK-21 cells in series, ordinarily, there is a tendency toward the cell number one day later. Consequently, GF-70 is added at the time of 48 hours after initiation of the culture. The progress of culture is as shown in FIG. 1 and there is the significant proliferation-stimulating effect, as compared with the control, observed for both cases of the GF-70 concentration levels of 10 μg/ml and 100 μg/ml.

The results of the three above described experiments suggest that GF-70 not only promote the nucleic acid synthesis but also processes the action of stimulating the cell multiplication itself.

Experiment 4: GF-70's action of stimulating the granulation as evaluated by the P.V.H.—sponge burying method.

Subcutaneously into the depilated abdomen of Wistar strain male rats (six-weeks aged) is buried a P.V.H.—sponge (polyvinyl hormonal sponge) absorbed with sterilized isotonic saline solution and isotonic saline solution containing GF-70 (2 mg/ml of GF-70), followed by removal of the buried sponge with time elapsed to measure its wet and dry weights. Table 3 indicates the results obtained on the 7th day after burying the sponge there is a significant difference (P<0.01) in the dry weight as well as the weight of newly grown granulation tissue between the group buried with the sponge absorbed with isotonic saline solution and the one with the sponge absorbed with isotonic saline solution containing GF-70. For comparative purposes, and taking into consideration the action of steroids to generally suppress proliferation of granulation, a similar experiment is conducted in this test with rats that are parenterally administered in advance with Prednisoline methyl acetate in an amount of 400 μg per 150 g of body weight. It can be seen from the results that, with the group administered with Prednisoline methyl acetate, the dry weight, wet weight, quantity of exudate and weight of newly grown granulation tissue all fall below those with the control, whereas addition of GF-70 to the group restricts the action of suppressing proliferation by the steroid, leading to the increases of the dry weight and weight of granulation tissue above the control.

TABLE 3

| | Non-treated group | | Steroid treated group** | |
|---|---|---|---|---|
| | Isotonic saline | Isotonic saline + GF-70 | Isotonic saline | Isotonic saline + GF-70 |
| (1) Wet weight, mg | 308.3 ± 86.6 | 362.1 ± 90.1 | 225 ± 58.9 | 272.4 ± 82.8 |
| % | 100 | 117.5 | 73.0* | 88.4 |
| (2) Dry weight, mg | 63.4 ± 13.2 | 80.3 ± 17.1 | 57.8 ± 9.9 | 69.9 ± 15.7 |
| % | 100 | 126.7* | 91.2 | 110.3 |
| (1)–(2) Liquid content, mg | 244.9 ± 74.6 | 281.8 ± 73.7 | 167.4 ± 52.2 | 202.9 ± 79.0 |
| % | 100 | 115.1 | 68.4* | 82.9 |
| (2) - sponge weight Solid content, mg | 28.0 ± 12.4 | 44.3 ± 16.6 | 22.6 ± 9.6 | 33.9 ± 15.2 |
| % | 100 | 158.2* | 80.7 | 121.1 |

Remarks:
*Statistical significance P < 0.01.
**0.4 mg of Prednisolone acetate Administered Experiment 5: Changes in the levels of DNA and RNA in the buried sponge in relation to GF-70.

Figure 2A:
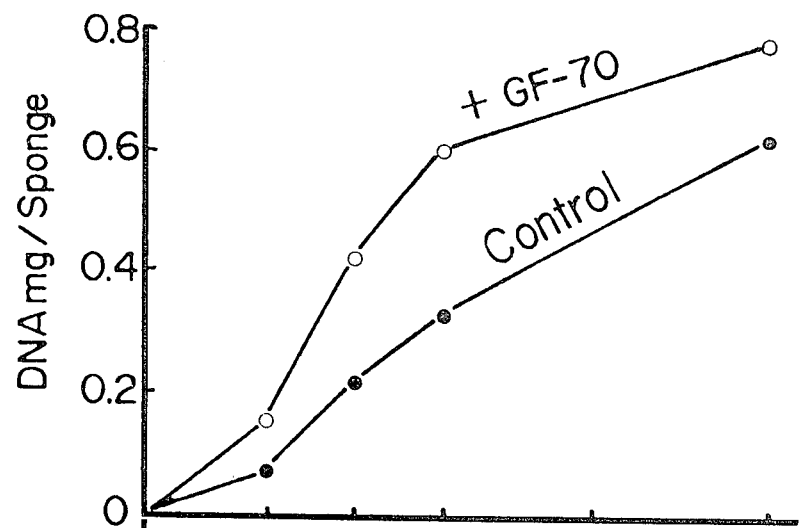
FIG. 2 is a graph showing the effects of GF-70 on quantities of DNA and RNA in the P. V. H.—sponge buried beneath the skin into the abdomen of a rat (DNA:2A, RNA:2B).
Figure 2B:
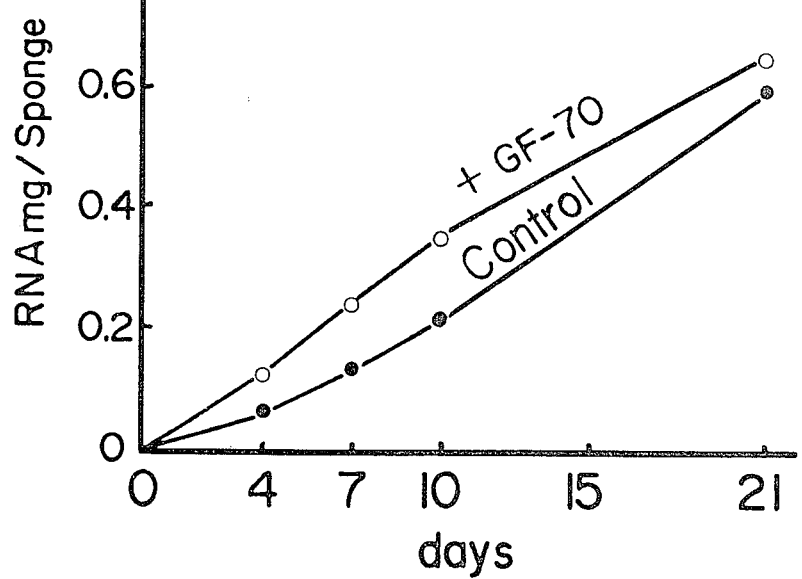

In accordance with the same method as described in Experiment 4, the levels of DNA and RNA in the P.V.H.—sponge buried subcutaneously into the abdomen of a rat are measured with time elapsed. As indicated in FIG. 2, there is developed, on the fourth day after burying the sponges, a significant difference in the DNA level for the GF-70 containing sponge as compared with the one containing the isotonic saline solution, with the difference being marked on the 10th day.

Similarly, an increase in the RNA level is shown to be brought about by GF-70. Consequently, it follows from this that GF-70 can produce the outstanding effect of stimulating the synthesis of both DNA and RNA. Nevertheless, stimulation of the DNA and RNA syntheses to be achieved by GF-70 is not unrestricted; initially, these syntheses proceed faster as compared with the control group, but reach the stage of being fixed in synthesized quantities both with the control and GF-70 groups after about three weeks pass, with no difference being observed between both of the groups thereafter. Accordingly, GF-70 is not judged to give rise to the disordered, unrestrained cell growth and nucleic acid synthesis like cancer cells.

Experiment 6: Changes in the weight of collagen in the buried sponge in relation to GF-70.

In the same manner as described in Experiment 5, P.V.H.—sponges impregnated with GF-70 at varying concentrations are buried beneath the skin into the abdomen of rats, followed removal of the sponges on the 4th and 7th days after being buried to measure new collagen growth as the weight of hydroxyproline per sponge in accordance with the method of Martin and Axelrod. As compared with the control sponges, a significant increase is found to be shown for the weight of collagen in the GF-70 containing sponges. A comparative study on the GF-70 heat-treated at 60° C. for 20 minutes for inactivation of enzyme activity and the egg albumin as the control reveals that they have a lessened growth effect on collagen, with no significant difference being created (refer to Table 4 below).

TABLE 4

| No. of days after burying P.V.H.-sponges | Hydroxyproline, µg/sponge (n = 8) | | | |
|---|---|---|---|---|
| | Control group | GF-70 group | Heat-treated GF-70 group | Albumin group |
| 4 | 125.5 ± 12.2 100% | 221.9 ± 17.6* 177% | 80 ± 8.7 63.7% | 132.3 ± 18.0 105% |
| 7 | 227.6 ± 32.4 100% | 580.9 ± 49.1** 255% | 354.0 ± 39.4 156% | 331.7 ± 18.8 146% |

Remarks
*P < 0.01
**P < 0.001

Experiment 7: Histological observation of buried sponges.

P.V.H.—sponges being buried in accordance with the method as described in Experiment 4 are taken out on the 7th day after being buried, being fixed with formalin, and subjected to Azan staining and Hematoxylin-Eosin staining, etc, to elucidate histologically the effects of GF-70 on the growth of granulation tissues.

As it serves to justify the results obtained in the Experiments 4 through 6, Hematoxylin-Eosin staining with the GF-70 containing sponges reveals that fibroblasts are existing in the inside of the sponges, in contrast to the control, and that the cells in pores of the sponges are dense. It is evident from these that GF-70 possesses the growing effect for newly grown granulation. In addition, Azan staining indicates that there exist collagen fibers in the inside, which implies that GF-70 exhibits the capability to stimulate the granulation (FIG. 5).

Experiment 8: Therapuetic effect of GF-70 on experimental wounds.

On the basis of the above mentioned experiments, the present inventors have gained confidence that GF-70 is effective for the granulation not only on the molecular level but also from a histological point of view, and proceeded further to making a hole of 5 mm in diameter by a punch on the dorsal skin of a Wistar-strain male rat to observe how the ointments shown below reduce the surface area of the wounded region. The GF-70 ointment utilized for this purpose is composed of GF-70 of 10 µmoles TMP formed /g ointment (10 µmoles TMP formed /mg protein) being added to the ointment base consisting of 66 parts of white vaseline, 3.5 parts of cetanol and 0.16 part of methylparaben. The GF-70 ointment and a commercially available wound treatment agent, X, are compared, and as shown below in Table 5, it can be seen that the GF-70 ointment promotes healing earlier by about 3 days with the significant difference, as compared with X.

TABLE 5

| | | (unit, mm²) | | | | | | | | |
|---|---|---|---|---|---|---|---|---|---|---|
| Group receiving ointment base | No. of days elapsed | 1 | 2 | 3 | 4 | 5 | 6 | 7 | 8 | 9 |
| | Wound area | 19.6 | 21.7 | 17.3 | 21.1 | 16.5 | 12.7 | 10.6 | 3.1 | 2.5 |
| Group receiving GF-70 | No. of days elapsed | 1 | 2 | 3 | 4 | 5 | 6 | 7 | 8 | 9 |
| | Wound area | 23.6 | 16.4 | 13.0 | 15.1 | 10.6 | 5.4 | 0 | 0 | 0 |
| Group receiving X | No. of days elapsed | 1 | 2 | 3 | 4 | 5 | 6 | 7 | 8 | 9 |
| | Wound area | 19.6 | 25.7 | 23.6 | 18.0 | 18.3 | 11.5 | 8.4 | 3.1 | 1.4 |

As described above, the GF-70 ointment achieves the remarkable, excellent effect on the wound healing. Yet, the further thorough examination has proved that GF-70 is particularly effective up to the stage of forming the granulation but possesses a relatively weak capability of epidermization being necessary for completion of wound healing. Furthermore, the additional research study carried out later reveals that, among a large number of medicinal agents for external application for treatment of wounds, zinc oxide exhibits especially the synergistic effect with GF-70 to stimulate the epidermization. GF-70 and zinc oxide are investigated from the standpoint of pathologic histology for their stimulating effect of epidermization, with the obtained results shown below in Experiment 9:

Experiment 9: Epidermization effect of GF-70 and zinc oxide.

The dorsal skin of a rabbit, after cutting the hair by use of an electric clipper, is depilated by a depilatory cream, disinfected with a 70% alcohol solution, and is peeled off to a thickness of 20/1000 inch the epidermis at the depilated region by means of a dermatome. The skin-removed area is divided into four equal parts, which are alloted to the ointment base part (A), zinc-oxide ointment part (B), GF-70 ointment part (C) and GF-70/zinc oxide ointment part (D), respectively, to treat with the corresponding ointment. Their healing progresses are compared on the 5th and 9th days.

Figure 5A:
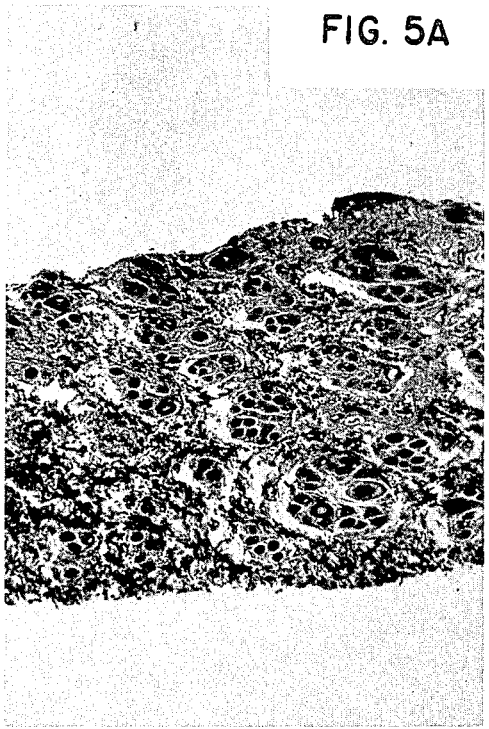
FIG. 5A–5D are photomicrographs showing the effects of GF-70 on the growth of granulation tissues in sponges.
Figure 5B:
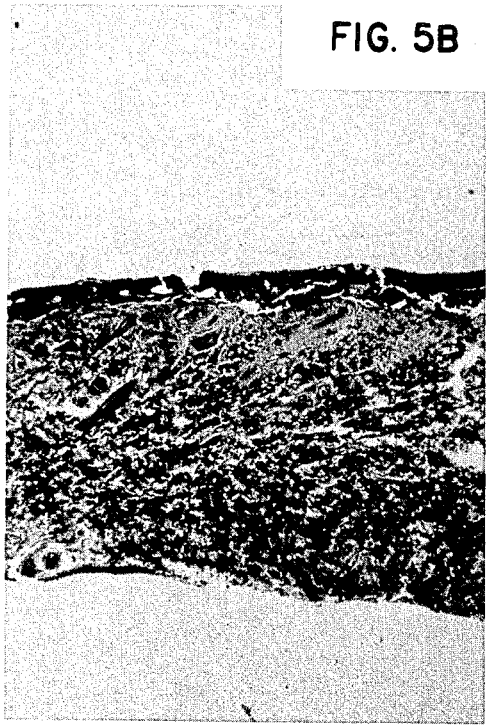
Figure 5C:
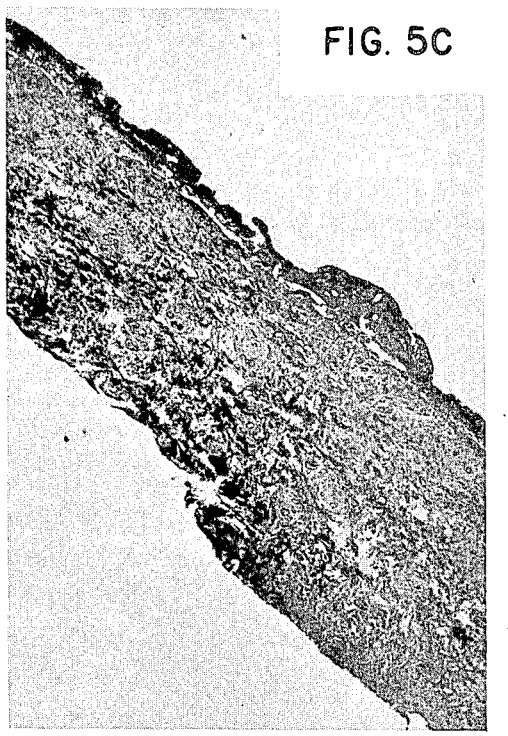
Figure 5D:
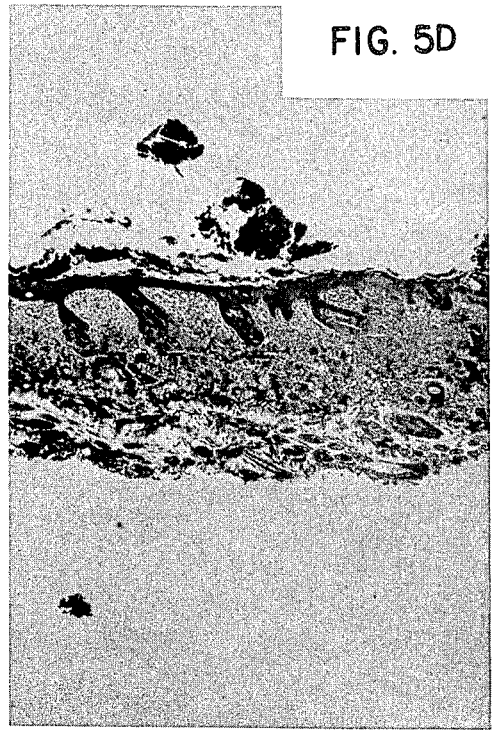

FIG. 5 shows microscopic photographs of the tissue taken on the 5th day, wherein a marked epidermization is indicated in FIG. 5D.

The effect achieved by the combined use of GF-70/zinc oxide as shown above is evidenced by a number of animal tests conducted following the above experiment.

Figure 3:
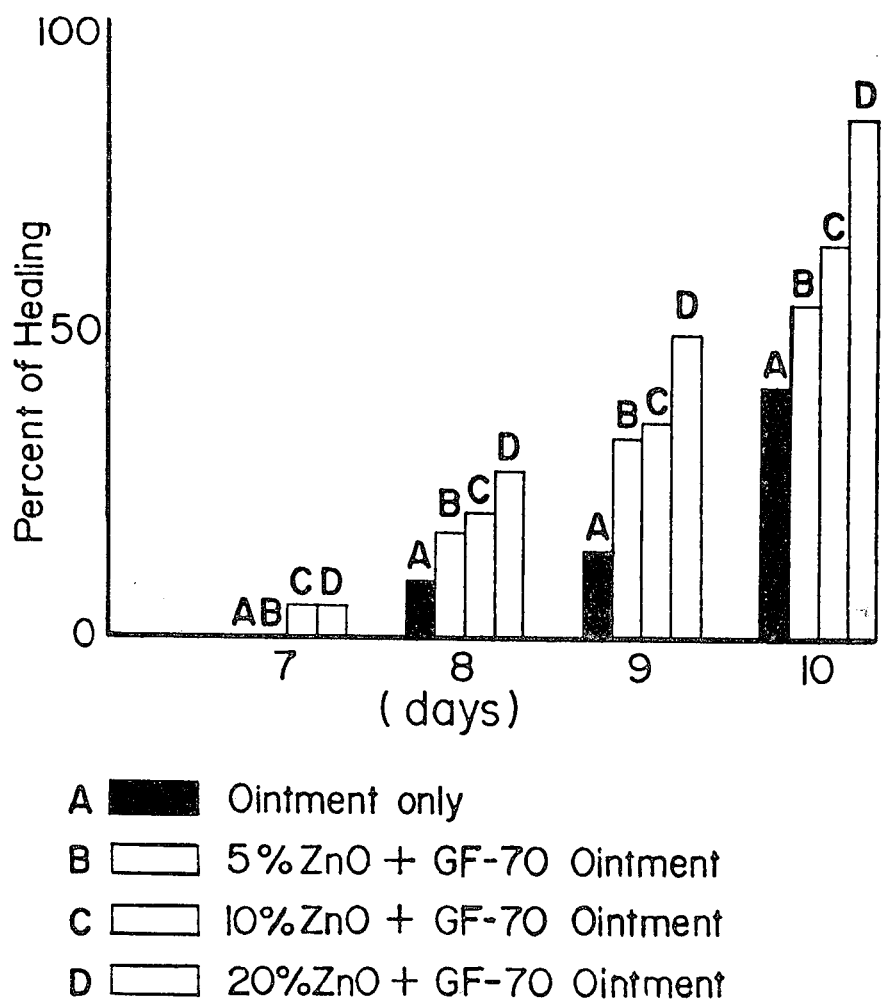
FIG. 3 is a graph showing the effects of the concentration of zinc oxide formulated in relation to GF-70 in the treatment of the experimental wounds.

A bar-graph illustration of the incidence of complete healing in one experiment each with the use of (A) an ointment base alone (the base as described hereinabove) (B) the GF-70 ointment (10 mg/g of GF-70 content in the ointment), (C) the ointment composed solely of zinc oxide (20% of zinc oxide content) and (D) the GF-70/zinc oxide containing ointment (the same contents of GF-70 and zinc oxide as described above), whereby the effect by the combined use of GF-70 and zinc oxide can be evidently noted, shows that the healing ratio observed after 10 days is in the order of D:100%>B:85%>C:72%>A:65%, or the ointment composed in combination of GF-70 and zinc oxide is the most efficacious, being followed by the one comprised solely of GF-70. In the meanwhile, it is true that the higher the content of zinc oxide, the earlier the healing is completed, but the content of zinc oxide in excess of 40% results in ointments representing the hard and brittle state as the whole and not assuming the ointment appearance, thereby bringing about the difficulty in putting ordinary ointment bases into practical use. Yet, utilization of excipients being liquid per se at ambient temperature, such as liquid paraffin, liquid oils and fats (for example, liquid oils with a higher content of unsaturated fatty acids such as olive oil, peanut oil and cotton seed oil), and polyethylene oxide with a low polymerization degree, may enable the content of zinc oxide to increase up to 60% or more. FIG. 3 shows the summary of results of other experiment where quantities of zinc oxide formulated in the above mentioned excipient in combination with GF-70 are varied from 5% to 20%; a tendency is conspicuously revealed that at the constant weight of GF-70, the incidence of complete healing increases with the rising quantity of zinc oxide. Judging from the Figure, quantities of zinc oxide are, preferably, at least 20% or more against the excipient.

In cases of major surgical procedures undergone and serious injuries sustained, a large blood loss takes place inevitably, resulting in reduced oxygen supply to tissues and generalized asthenia which bring about naturally changes in the healing mechanism. FIG. 5 shows the accumulated healing ratio for wounds obtained with rats having been subjected to bloodletting to cause an anemic state, whereby the superiority of the ointment (D) containing GF-70 and zinc oxide is distinctly noted. The ointment composed solely of GF-70 (B), for which the healing ratio is kept good up to the 2nd day, then trending to remain flat or deteriorate thereafter until around 5th day, and rises rapidly thereafter, eventually produces the effect practically equal to the one composed of zinc oxide alone (C). A higher healing ratio in the initial through intermediary treatment stages after wound infliction, realized by GF-70 or especially its mixture with zinc oxide, suggests that GF-70 exhibits the excellent capability to promote healing during the diminished physiological function brought about by phlebotomy. Shown for reference in Table 6 are the results obtained by subjecting to the t-test the records of the healing experiment conducted with rats having undergone phlebotomy.

TABLE 6

| No. of days treated t-Test | Ointment base group means ± SD | (SE) | Zinc oxide ointment group means ± SD | (SE) | GF-70 ointment group means ± SD | (SE) | GF-70/zinc oxide ointment group means ± SD | (SE) |
|---|---|---|---|---|---|---|---|---|
| 0 | 100 % | | 100 % | | 100 % | | 100 % | |
| 1 | 92.6 ± 9.3 | (3.1) | 90.5 ± 17.5 | (6.6) | 85.3 ± 12.9 | (4.3) | 72.4 ± 7.4 | (2.5) |
| t | | | 0.281 | | 1.383 | | 5.076 | |
| 2 | 68.0 ± 12.3 | (4.1) | 81.8 ± 19.4 | (7.4) | 56.3 ± 10.7 | (3.6) | 57.6 ± 8.4 | (2.8) |
| t | | | 1.642 | | 2.151 | | 2.098 | |
| 3 | 69.0 ± 19.2 | (6.3) | 63.3 ± 14.1 | (5.3) | 53.3 ± 12.3 | (4.1) | 50.4 ± 9.3 | (3.1) |
| t | | | 0.797 | | 2.196 | | 2.761 | |
| 4 | 63.3 ± 12.4 | (4.2) | 62.1 ± 18.4 | (7.0) | 51.0 ± 13.1 | (3.2) | 43.1 ± 8.1 | (2.7) |
| t | | | 1.440 | | 2.042 | | 4.086 | |
| 5 | 60.7 ± 9.0 | (3.0) | 58.3 ± 19.0 | (7.2) | 53.1 ± 11.8 | (3.9) | 39.9 ± 6.2 | (2.1) |
| t | | | 0.307 | | 1.538 | | 5.689 | |
| 6 | 52.7 ± 12.1 | (4.1) | 37.9 ± 18.3 | (6.9) | 40.2 ± 12.6 | (4.2) | 27.5 ± 9.4 | (3.1) |
| t | | | 1.851 | | 2.148 | | 4.931 | |
| 7 | 40.2 ± 7.8 | (2.6) | 20.2 ± 13.9 | (5.3) | 23.0 ± 8.5 | (2.8) | 11.5 ± 5.2 | (1.7) |
| t | | | 3.395 | | 4.453 | | 9.133 | |
| 8 | 30.1 ± 12.8 | (4.3) | 14.9 ± 13.3 | (5.0) | 17.0 ± 5.7 | (1.9) | 7.85 ± 4.5 | (1.5) |
| t | | | 2.287 | | 2.801 | | 4.891 | |
| 9 | 15.4 ± 5.6 | (1.9) | 7.4 ± 7.1 | (2.7) | 9.13 ± 5.3 | (1.8) | 3.45 ± 2.7 | (0.9) |
| t | | | 2.459 | | 2.455 | | 5.830 | |
| 10 | 11.3 ± 6.7 | (2.3) | 2.6 ± 4.5 | (1.7) | 4.1 ± 3.6 | (1.2) | 1.13 ± 1.5 | (0.5) |
| t | | | 3.093 | | 2.849 | | 4.429 | |

The present invention is based on the finding as described hereinbefore, and an essential feature resides in a wound treatment agent containing as the essential effective ingredients GF-70, solely, which is obtained from a broth (bacterium body and filtrate) or NPT producing bacterium belonging to the genus Clostridium, or in combination with zinc oxide. As described previously, NPT is existing in bacterium bodies and culture medium liquids (especially, in larger quantities in the former), and its production is the most active during the exponential phase in which the growth of bacteria is vigorous. Consequently, cultivation should be suspended within the exponential phase, followed by treating with a hydrophilic solvent such as acetone and alcohol to kill the bacterium and isolating the NPT fraction from the bacterium bodies and/or filtrate. Isolation, as being described in detail in the specification of the Japanese Pat. No. 745940, is conducted suitably by the use of the known means for purification of proteins, solely or in combination, whereby the object of the present invention can be achieved even when purification up to an exceedingly high degree of purity is not realized.

The wound treatment agent according to the present invention is usable in various forms as a medicine for external application. The simplest form is to apply to lesions GF-70 together with an appropriate pharmaceutically acceptable carrier in the form of a solution; or, it can be dusted into lesions in the form of a dry powder. Still, the most general is to apply it to lesions in the form of an ointment. To this end, usable are all of known hydrophobic or hydrophilic ointment excipients such as vaseline, lanolin, cetanol, bee wax, Carbowax (polyethylene oxide) and oils and fats of animal and plant origins. So as not to affect adversely the stability of the enzymes, however, it is desirable to avoid the use of excipients composed mainly of water. A variety of additives, and particularly zinc oxide, are essential elements to convert the present invention into preferable embodiments, and other additives, for example vitamin A, bactericides not inhibiting the activity of NPT (e.g. methylparaben), antibiotics, perfumes, etc., may be added if desired. The quantity of GF-70 to be contained in preparations should preferably be varied depending on magnitude of the potencies of the said fraction, and, for the ones with more than 10 in specific activity, it is suggested as the standard practice to add them at a rate of 0.05 to 1.0% against the preparations. It should be noted that an addition rate of more than 1.0% does not increase the healing effect to such an extent as expected. Addition is usually carried out by mixing while adding little by little to an excipient GP-70 in the form of powder or after dissolving in a small amount of water. Other ingredients such as zinc oxide are mixed into the excipient simultaneously or separately, whereby the mixing means therefor may be conducted into practice in accordance with the general production procedures for ointments. As hereinbefore mentioned, formulation of zinc oxide in larger quantities is desirable in increasing the therapeutic efficacy of the product according to the present invention, whereas, on the other hand, it enhances the viscosity of preparations and even suffers the disadvantage of losing the plasticity of the products in the case of extremely excessive addition; in such a case, replacement should be made with excipients being less viscous per se, or sometimes excipients consisting of per se fluid oils and fats, low-molecular-weight polyethylene oxide, liquid paraffin, etc.

Below described is an example of embodiment (an example of processing into a preparation), while, as already evident, the object of the present invention lies in utilization of GF-70 or its mixture with zinc oxide as a medicine for external application for the treatment of wounds, ulcers, etc., and needless to say, the following example is not intended to limit the technical scope of the invention:

[Example of Processing into a Preparation]

Fifty grams of purified lanolin, 50 g of bleached bee wax and 900 g of white vaseline are mixed and kneaded under warming by a mixing machine to produce an excipient (I). 200 g of zinc oxide is kneaded into 70 g of purified lanolin, followed by adding 730 g of the excipient (I) to mix and knead again under warming, thus yielding as excipient (II) which is allowed to cool to room temperature. Then, 28 mg of GF-70 (freeze-dried product with 3.5 $\mu$moles/mg of specific activity) being dissolved in 10 ml of sterilized distilled water is added to 1 kg of the excipient (II) to knead and mix, thus resulting in about 1 kg of a GF-70/zinc oxide ointment product.

What is claimed is:

1. A wound treatment preparation comprising: an effective wound treating amount of nucleoside phosphotransferase produced by a nucleoside phosphotransferase producing bacterium of the genus clostridium as the effective ingredient and a pharmaceutically acceptable topical carrier.

2. A wound treatment preparation according to claim 1, and further including an effective amount of zinc oxide.

3. A wound treatment preparation according to claim 1, in the form of an ointment.

4. A wound treatment preparation according to claim 2, in the form of an ointment.

5. A wound treatment preparation according to claim 1 or 2, having a pH of from 6.0 to 8.0.

6. A wound treatment preparation according to claims 1 or 2 in the form of a solution.

7. A wound treatment preparation according to claims 1 or 2 in the form of a powder.

8. A wound treatment preparation according to claim 2, wherein said zinc oxide is present in an amount of 5–20% by weight of the preparation.

9. A wound treatment comprising: applying an effective wound healing promoting amount of a preparation including nucleoside phosphotransferase produced by bacterium of the genus Clostridium and a pharmaceutically acceptable carrier topical to the wound area.

10. A method according to claim 9, wherein said preparation further includes an effective amount of zinc oxide.

11. A wound treatment method according to claim 10, wherein said zinc oxide is present in an amount of 5–20% by weight of the preparation.

12. A wound treatment method according to claim 10, wherein said zinc oxide is present in an amount of up to 60% by weight of the preparation.

* * * * *